United States Patent
Smith et al.

(10) Patent No.: US 6,779,522 B2
(45) Date of Patent: Aug. 24, 2004

(54) METHOD AND APPARATUS FOR TREATING BREATHING GASES

(75) Inventors: T. Paul Smith, Oakhurst, NJ (US); David A. Leighty, Beachwood, NJ (US); Charles E. Dubois, Wall Township, NJ (US); Erik M. Anhorn, Jackson, NJ (US)

(73) Assignee: Perma Pure, Inc., Toms River, NJ (US)

( * ) Notice: Subject to any disclaimer, the term of this patent is extended or adjusted under 35 U.S.C. 154(b) by 156 days.

(21) Appl. No.: 09/978,131

(22) Filed: Oct. 16, 2001

(65) Prior Publication Data

US 2003/0070680 A1 Apr. 17, 2003

(51) Int. Cl.[7] ............................................. A61M 15/00
(52) U.S. Cl. ........................... 128/203.16; 128/203.26; 128/204.16; 128/205.12; 128/911
(58) Field of Search ................... 128/203.16, 203.26, 128/204.16, 205.12, 911; 156/83–85, 244.13; 264/515, 563, 565

(56) References Cited

U.S. PATENT DOCUMENTS

| | | | | |
|---|---|---|---|---|
| 3,196,194 A | * | 7/1965 | Ely, Jr. et al. | 264/558 |
| 3,296,343 A | * | 1/1967 | Buttolph et al. | 264/565 |
| 3,547,272 A | * | 12/1970 | Shaines et al. | 210/321.87 |
| 3,558,764 A | * | 1/1971 | Isaacson et al. | 264/565 |
| 3,616,796 A | * | 11/1971 | Jackson | 128/203.27 |
| 3,735,558 A | * | 5/1973 | Skarstrom et al. | 95/51 |
| 3,912,795 A | * | 10/1975 | Jackson | 261/36.1 |
| 4,243,629 A | * | 1/1981 | Tramezzani | 264/563 |
| 4,705,543 A | * | 11/1987 | Kertzman | 96/6 |
| 4,767,426 A | * | 8/1988 | Daly et al. | 55/487 |
| 4,799,374 A | * | 1/1989 | Bossart et al. | 250/343 |
| 4,808,201 A | * | 2/1989 | Kertzman | 96/10 |
| 4,896,904 A | * | 1/1990 | Gadsden et al. | 285/381.5 |
| 5,042,500 A | * | 8/1991 | Norlien et al. | 600/532 |
| 5,053,116 A | * | 10/1991 | Mayer | 204/406 |
| 5,980,795 A | * | 11/1999 | Klotzer et al. | 264/41 |
| 5,996,976 A | * | 12/1999 | Murphy et al. | 261/104 |
| 6,015,516 A | * | 1/2000 | Chung et al. | 264/41 |

* cited by examiner

*Primary Examiner*—Aaron J. Lewis
(74) *Attorney, Agent, or Firm*—Robert M. Skolink

(57) ABSTRACT

A method of making thin-walled permeable tubing using air blown extrusion, and of using the tubing in a device which enables a substantial humidification or drying of patient breathing gases in the breathing lines for patient monitoring or anesthesia results in cost savings and increased efficiency.

6 Claims, 1 Drawing Sheet

METHOD AND APPARATUS FOR TREATING BREATHING GASES

BACKGROUND OF THE INVENTION

1. Field of the Invention

The present invention relates to methods and apparatus for drying or humidifying breathing gases supplied to a patient during administration of gas anesthesia, or during administration of artificial respiration or of supplemental oxygen when a patient has difficulty breathing.

2. Description of the Related Art

Commonly assigned U.S. Pat. Nos. 3,735,558, 4,705,542, and 4,808,201 disclose and claim devices having tubes constructed of permeable materials selected so the humidity and temperature of gases flowing through the tubes equalizes to those of gases surrounding the outside of the tubes. The tubes are formed of extrudable plastic materials that selectively permit water to diffuse through the tube walls, but inhibit the ability of other gases from so diffusing. Water diffuses through the tube walls from the side of higher concentration to that of lower concentration. A difference in total pressure between the inside and the outside of the tubes is not required, only a difference in water concentration. In practice, when highly humid gas passes through the tubes, water vapor in the gas diffuses through the tube walls out into the surrounding dry air or gas.

Circulation of a surrounding dry air or gas permits continuous operation of the process. Thus, condensation in the tubing and downstream of the tubing are prevented from occurring, and the problems occasioned by such condensation are eliminated. Because of extreme selectivity in the process, only water is removed, not other gases of interest.

a) Drying

At some points in the "breathing circuit" that recirculates breathing gases to a patient, there is excess water. Condensation forms (referred to as rain-out). This condensation creates flow and contamination problems and should be avoided, or removed when it occurs. An example of a point where rain-out occurs is immediately after the patient, because the patient exhales breath that is water-saturated. When exhaled breath cools even slightly inside a breathing circuit, rain-out occurs.

Another example at a different point in the circuit is after the carbon dioxide scrubber. Anesthesia machines recirculate breathing gases from the machine through the patient and back. Side-stream measurements are made of the oxygen, carbon dioxide, and anesthetic gas levels in the breath. Based on these measurements the anesthesia machine adds oxygen and anesthetic agent consumed by the patient, but the machine must remove excess carbon dioxide added by the patient. Soda-lime is used to absorb and chemically remove this excess carbon dioxide from the exhaled breath of the patient. In the process of removing carbon dioxide, soda lime releases water. This excess water causes rain-out in the breathing circuit immediately after the soda-lime scrubber.

No satisfactory solution currently exists for these drying applications. The best alternative is a device called an HME, or heat and moisture exchanger. It is in essence an absorptive pad similar to a sponge placed at a point near the patient's mask where exhaled breath passes one way through it, then inhaled breath passes in the opposite direction. This device recovers some of the excess heat and water from the exhaled breath of the patient and transfers it to the inhaled breath. It does not remove enough water, and it cannot be used after the soda-lime scrubber because at this location there is no reverse flow of dry breathing gas to remove the retained water.

b) Humidifying

While in some locations within the breathing circuit the breathing gases are too wet and need drying, by the time the breathing gas returns to the patient it is too dry and needs to be humidified. Otherwise, the air passages of the patient become excessively dry.

The existing solutions have drawbacks. The HME mentioned above does not humidify enough. Bubblers and boilers are hard to control and add liquid water droplets, causing rain-out. Bubblers are very noisy (disturbing the patient), while boilers pose a burn and electrical hazard.

Existing medical dryers and humidifiers that utilize the permeation technology described herein are inadequate for this task. The existing dryers contain one strand of small-bore tubing (typically 0.050 to 0.060 inch outer diameter) that can process only a small sample of the total breath gas stream. This sample is removed through a side port and used for testing of the concentration of gases in the breath (hence the term side-stream sampling). Moisture within the breath permeates through the walls of the tubing and pervaporates into the surrounding ambient air. When the breath comes to equilibrium with room humidity, it is dry enough for this application, so it is unnecessary to supply a source of dry air to surround the tubing to remove water. The tubing may be surrounded by a protective braiding of plastic mesh to prevent damage or contamination with skin oils when handled. When liquid water or humid air or gas surrounds the outside of the tubing instead of dry air, the device operates in reverse as a humidifier.

The tubing in these small devices is sufficiently strong to be self-supporting (does not collapse under its own weight), but it is too narrow to process the entire flow of breathing gases to a patient. These small devices process a flow of up to 0.25 liters per minute with adequate drying. The full flow of breathing gases is up to 40 liters per minute, and this is far too high for these small devices to process. Not only is there insufficient drying (or humidifying) capacity, but there is also far too much pressure restriction to such a high flow.

The existing device cannot be simply scaled to a sufficiently large size to satisfy the new applications of drying or humidifying the full breathing gas stream (treatment of the process gas) rather than simply drying or humidifying a small sample of the total flow (sample conditioning rather than process treatment). In the present design, as the tubing increases in diameter its walls must be made thicker so it will continue to support its own weight. As the walls become thicker water takes longer to permeate through them, so there are diminishing returns; consequently, using large-bore, self-supporting tubing for this application is impractical. Also, the NAFION® polymer currently used to form the permeable tubing is extremely expensive, so larger diameter self-supporting tubing with concomitant thicker walls is prohibitively expensive.

SUMMARY OF THE INVENTION

The present invention is an oversized version of the device described above. The same product is used for both drying and humidifying applications, just operated in reverse. It involves using NAFION® tubing that is so thin-walled it will not support its own weight. Plastic mesh tubing or other similar suitably porous material is inserted inside the NAFION® tubing to hold it open. Another piece of plastic mesh tubing or similar suitably porous material may be installed over the outside of the NAFION® tubing to protect it from damage or from contamination by skin oils during handling. This approach permits use of large-bore tubing suitable for use in breathing circuits, typically 15 mm (0.6 inch) in outer diameter.

Because the NAFION® tubing in the invention has very thin walls, water permeates through it very quickly, so it can process high flows of breath. Because the walls are very thin (typically 0.002–0.003 inch), there is much less NAFION® used, so the cost of the device is within acceptable limits for medical use as a disposable device (single-use or limited re-use). Because it has a larger diameter, there is less pressure restriction. Much of the breathing circuit is 15 mm (0.6 inch) in diameter, the same as this NAFION® tubing, so there is no more pressure restriction in the invention than in the rest of the circuit.

The completed device includes fittings on each end of the tubing that permit it to be conveniently connected into the breathing circuit. The device is designed to incorporate the fittings in such a way that gas-tight seals are made at the fittings, and the supporting mesh is locked into the fitting so that it becomes a single, semi-rigid structural unit. The test devices are about 6 inches long, but can in principle be any length.

The NAFION® tubing is fabricated by a process known as blown-film extrusion. This process involves the following steps, which are akin to making trash bags, a material that has walls that are also far too thin to support their own weight. Typical trash bags have a wall thickness of 0.002 or 0.003 inch (HEFTY® trash bags may be a bit thicker). The new tubing is typically 0.0025 inch in wall thickness, just like trash bags. Just like a trashcan holds the trash bag open, the mesh insert holds the tubing open from the inside rather than from the outside. The mesh is sufficiently coarsely woven so that it does not interfere with free circulation of gases to the surface of the tubing.

The method for making the thin-walled tubing consists of several steps, starting with NAFION® in a pelletized form. The raw material is fed into an extruder. The material is forced through a set of concentric extruding heads while air, at a specified rate, is blown through the center to create a thin-walled tube. The tubing then undergoes a chemical treatment process to convert it from its original, thermoplastic form to the hydrogen-ion form that is water-permeable. The final step involves drying the tubing in a controlled environment.

Inserting the NAFION® tubing in the outer protective mesh is the first assembly step in making the product of the invention. The inside diameter of the outer mesh is slightly larger than the outside diameter of the tubing so the NAFION® fits through the center of the mesh. Because of the tube's thin-wall and non-self supporting nature, the tubing can be folded to make feeding it through the inside of the outer protective mesh easier.

After the tubing and outer mesh assembly is created the end fittings are attached one end at a time. The outer mesh, on one end, is pushed back slightly to expose the NAFION® tube. The exposed end of the NAFION® is soaked in water which causes it to expand. The end fitting is inserted inside the expanded tubing. The NAFION® tube is then heated slightly to dry and shrink the tubing back to its' original dimensions. At this point a piece of plastic, adhesive-lined, heat shrinkable tubing is placed on the outside of the tubing and end fitting assembly. The heat shrinkable tubing is located so as to overlap the intersection of the NAFION® and end fitting. The adhesive-lined heat shrink tubing is then shrunk to create a leak tight seal between the NAFION® tubing and the end connector. The outer protective mesh is re-positioned and the above procedure is repeated on the opposite end of the assembly.

With both end fittings connected and sealed to the NAFION® tube with heat shrink, the outer protective mesh is attached to the end fitting/tubing assembly. The mesh is evenly positioned over the assembly and a piece of adhesive-lined heat shrink is placed over the outer mesh, tubing and end fitting assembly on both ends. The heat shrink tubing is then shrunk which fixes the outer protective mesh in its' final position.

The final step in the assembly process is inserting the inner protective mesh inside the existing assembly. The outside diameter of the inner protective mesh is slightly smaller than the inside diameter of the NAFION® tubing so when the inner mesh is inserted into the assembly there exists an interference fit between the tubing and the inner mesh. This interference fit is enough to hold the inner protective mesh in place.

BRIEF DESCRIPTION OF THE DRAWINGS

These as well as further objects and advantages of the invention will become apparent to those skilled in the art from a review of the following detailed specification reference being made to the accompanying drawings in which.

DETAILED DESCRIPTION OF THE INVENTION

Figure 1:
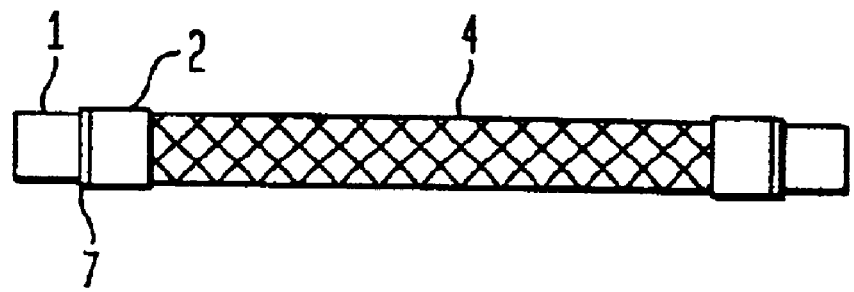
FIG. 1 is a side view of the apparatus of the present invention.
Figure 2:
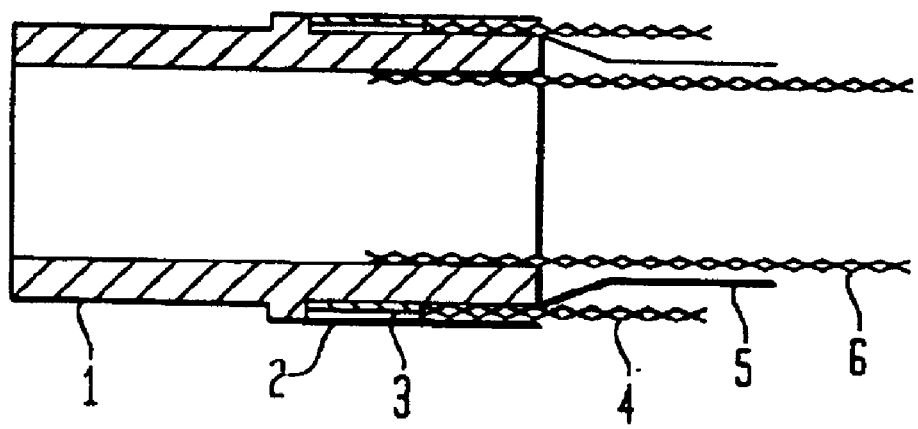
FIG. 2 is a sectional view of one end of the apparatus shown in FIG. 1.

The apparatus of the present invention is shown in FIGS. 1–2. Thin walled NAFION® tubing 5 is supported by outer protective mesh 4 and inner protective mesh 6. The supporting meshes 4 and 6 extend over the entire length of the NAFION® tubing. Heat shrinks 2 and 3 are plastic, adhesive-lined heat shrinkable tubing Connector 1 is a hollow cylindrical structure formed of materials such as polypropylene, polyethylene, PVC, or polycarbonate. The connector 1 has a shoulder 7 formed thereon for supporting the edges of the inner and outer heat shrinks 2 and 3.

A further understanding of the present invention may be had by reference to the following examples of the method of fabrication of the thin walled tubing and the fabrication of the structure shown in FIGS. 1–2.

EXAMPLE 1

NAFION® tubing having a wall thickness of 0.0025"±0.005" was formed employing an extruder known as a Micro Blown Film Extruder, Model No. Microtruder RCP-0625-BF, manufactured by Randcastle Extrusion Systems Inc. of Cedar Grove, N.J. The quantity of 0.004 lbs./foot of NAFION® in pelletized form was fed into the extruder. The material was forced through the set of concentric extruding heads in the extruder while air was blown through the center to create a thin-walled tube. The resultant product is a flat band, which is stored on a roll.

The tubing then undergoes a known process described in Dupont Technical Bulletin NAE302.

The next step is drying the tubing in a controlled environment at 25°–32° C. at 40%–50% relative humidity for 24–72 hours.

As the tubing is flat, it is bathed in methanol, which swells the material so that it can manually be manipulated to a tubular shape.

EXAMPLE 2

The thin walled tubing formed in accordance with Example 1 is used to fabricate the apparatus of FIGS. 1–2.

Inserting the NAFION® tubing in the outer protective mesh is the first assembly step in making the product of the invention. The inside diameter of the outer mesh is slightly larger than the outside diameter of the tubing so the NAFION® fits through the center of the mesh. Because of the tube's thin-wall and non-self supporting nature, the tubing can be folded to make feeding it through the inside of the outer protective mesh easier.

After the tubing and outer mesh assembly is created the end fittings are attached one end at a time. The outer mesh, on one end, is pushed back slightly to expose the NAFION® tube. The exposed end of the NAFION® is soaked in water which causes it to expand. The end fitting is inserted inside the expanded tubing. The NAFION® tube is then heated slightly to dry and shrink the tubing back to its original dimensions. At this point a piece of plastic, adhesive-lined, heat shrinkable tubing is placed on the outside of the tubing and end fitting assembly. The heat shrinkable tubing is located so as to overlap the intersection of the NAFION® and end fitting. The adhesive-lined heat shrink tubing is then shrunk to create a leak tight seal between the NAFION® tubing and the end connector. The outer protective mesh is re-positioned and the above procedure is repeated on the opposite end of the assembly.

With both end fittings connected and sealed to the NAFION® tube with heat shrink, the outer protective mesh is attached to the end fitting/tubing assembly. The mesh is evenly positioned over the assembly and a piece of adhesive-lined heat shrink is placed over the outer mesh, tubing and end fitting assembly on both ends. The heat shrink tubing is then shrunk which fixes the outer protective mesh in its final position.

The final step in the assembly process is inserting the inner protective mesh inside the existing assembly. The outside diameter of the inner protective mesh is slightly smaller than the inside diameter of the NAFION® tubing so when the inner mesh is inserted into the assembly there exists an interference fit between the tubing and the inner mesh. This interference fit is enough to hold the inner protective mesh in place.

As will be apparent to those skilled in the art, further modifications to the methods and apparatus of the invention may be made without departing from the spirit and scope of the invention; accordingly, what is sought to be protected is set forth in the appended claims.

We claim:

1. The method of manufacturing thin-walled permeable membrane tubing comprising the steps of: inserting water permeable material into a blown film extruder; forcing said material through concentric extruding heads in said extruder; blowing air through the center of said extruding head to create a thin-walled tube in the form of a flat band, converting said thin-walled tube to the hydrogen ion form; drying said converted flat band; bathing said flat band in methanol to swell said flat band; and manipulating said swelled band into a tubular shape.

2. The method of claim 1 wherein said material is in pelletized form when it is fed into said blown film extruder.

3. The method of claim 1 further including the steps of: inserting said tubular material an outer protective mesh; affixing end fittings to said tubular material by, at either end of said tubular material; exposing a portion of said tubular material by pushing back said outer protective mesh; soaking said portion in water to expand said portion; placing an end fitting inside said expanded portion; shrinking said expanded portion over said end fitting; and sealing said portion to said fitting.

4. The method claim 3 wherein the inside diameter of said outer mesh is larger than the outside diameter of the tubing.

5. The method of claim 3 wherein said expanded portion is sealed to said fitting by placing a plastic, adhesive-lined, heat shrinkable tube the outside of the tubing and end fitting assembly; and heat shrinking the tube over said end fitting assembly.

6. The method of claim 5 further including the steps of: placing an outer protective mesh over said tubing; placing adhesive-lined heat shrink material over said outer mesh; and heat shrinking said heat shrink material over said outer protective mesh.

* * * * *